(12) United States Patent
Fontaine et al.

(10) Patent No.: US 9,492,304 B2
(45) Date of Patent: Nov. 15, 2016

(54) ORTHOPEDIC DEVICE FOR MECHANICAL TREATMENT OF HALLUX VALGUS

(75) Inventors: Thierry Fontaine, Courrieres (FR); Cedric Gantie, Lagardelle sur Leze (FR)

(73) Assignee: SARL Pody Concept, La Madeleine (FR)

( * ) Notice: Subject to any disclaimer, the term of this patent is extended or adjusted under 35 U.S.C. 154(b) by 218 days.

(21) Appl. No.: 13/583,758

(22) PCT Filed: Mar. 10, 2011

(86) PCT No.: PCT/IB2011/051013
§ 371 (c)(1),
(2), (4) Date: Nov. 16, 2012

(87) PCT Pub. No.: WO2011/111019
PCT Pub. Date: Sep. 15, 2011

(65) Prior Publication Data
US 2013/0060181 A1    Mar. 7, 2013

(30) Foreign Application Priority Data
Mar. 10, 2010   (FR) ..................................... 10 00958

(51) Int. Cl.
*A61F 5/00*      (2006.01)
*A61F 5/01*      (2006.01)
(Continued)

(52) U.S. Cl.
CPC ............. *A61F 5/019* (2013.01); *A61F 13/064* (2013.01); *A61F 13/068* (2013.01); *A61F 2013/00697* (2013.01); *A61F 2013/00723* (2013.01)

(58) Field of Classification Search
CPC .................... A61F 5/019; A61F 5/0111; A61F 5/0113; A61F 5/0585; A61F 5/0102;
(Continued)

(56) References Cited

U.S. PATENT DOCUMENTS 826,515 A * 7/1906 Litch ............................... 602/30
1,175,718 A * 3/1916 Crowe .................... A61F 5/019
128/894

(Continued)

FOREIGN PATENT DOCUMENTS

DE    9206317 U1 * 7/1992 ............. A61F 5/019
FR    2576209 A1    7/1986
(Continued)

OTHER PUBLICATIONS

Int'l Search Report issued Jul. 19, 2011 in Int'l Application No. PCT/IB2011/051013; Written Opinion.

(Continued)

*Primary Examiner* — Kim M Lewis
(74) *Attorney, Agent, or Firm* — Panitch Schwarze Belisario & Nadel LLP

(57) ABSTRACT

An orthopedic device is provided for treatment of Hallux Valgus. The orthopedic device includes a main part (3) in the form of an elastic sleeve, intended to exert a restraining force (F1) locally on the metatarsals (M1, M2, M3, M4, M5), a distal part (5) for encapsulating the big toe, and a connecting band (6) between the main part (3) and the distal part (5), intended to be tensioned in order to exert a lateral force (F2) on the big toe that is directed inwards in relation to the axis Δ of the human body. A pad (4) is secured to the inner wall of the device, creating a localized increased thickness, and arranged to be positioned against the first metatarsal of the big toe. The pad acts as an anchor during the application of the lateral force, in different positions of (Continued)

the foot, thus allowing the tensile force on the connecting band (6) to be adjusted. The combined restraining and lateral forces serve to re-align the joint during walking.

35 Claims, 7 Drawing Sheets

(51) Int. Cl.
*A61F 13/06* (2006.01)
*A61F 13/00* (2006.01)

(58) Field of Classification Search
CPC ............... A61F 5/05875; A61F 13/064; A61F 13/068; A61F 13/065; A61F 2013/00697; A61F 2013/00723; A61F 13/063; A61F 13/069
USPC ................... 602/30, 31, 22, 60–66; 36/140; 128/882, 892–894; D24/190–192
See application file for complete search history.

(56) References Cited

U.S. PATENT DOCUMENTS

| | | | | |
|---|---|---|---|---|
| 1,373,211 A * | 3/1921 | Tanner | ............................. | 602/30 |
| 1,497,151 A * | 6/1924 | Malkin | ................... | A61F 5/019 |
| | | | | 128/893 |
| 1,538,026 A * | 5/1925 | Cramer | ........................... | 602/66 |
| 1,665,030 A * | 4/1928 | Hartwig | ................. | A61F 5/019 |
| | | | | 602/30 |
| 1,668,459 A * | 5/1928 | Levitt | ............................. | 602/66 |
| 1,746,865 A * | 2/1930 | Page | ....................... | A61F 5/019 |
| | | | | 602/30 |
| 1,785,185 A * | 12/1930 | Day | ........................ | A61F 5/019 |
| | | | | 602/30 |
| 2,033,609 A * | 3/1936 | Budin | ..................... | A61F 5/019 |
| | | | | 602/30 |
| 2,596,038 A * | 5/1952 | Mayer | ............................. | 602/30 |
| 3,049,120 A * | 8/1962 | Marcus | .................. | A61F 5/019 |
| | | | | 602/30 |
| 3,063,446 A * | 11/1962 | Levitt | ..................... | A61F 5/019 |
| | | | | 602/30 |
| 4,632,103 A * | 12/1986 | Fabricant et al. | .............. | 602/30 |
| 4,644,940 A * | 2/1987 | Nakamura | ....................... | 602/30 |
| 5,098,421 A * | 3/1992 | Zook | ............................. | 604/367 |
| 5,282,782 A * | 2/1994 | Kasahara | ................. | A61F 5/019 |
| | | | | 602/30 |
| 5,416,823 A * | 5/1995 | Livingston | .................... | 378/166 |
| 5,437,616 A * | 8/1995 | Kasahara | ................. | A61F 5/019 |
| | | | | 128/894 |
| 5,497,789 A | 3/1996 | Zook | | |
| 6,093,163 A * | 7/2000 | Chong | .................... | A61F 5/019 |
| | | | | 602/30 |
| 6,315,749 B1 * | 11/2001 | Sunayama | ............ | A61F 5/0111 |
| | | | | 128/882 |
| 7,396,338 B2 * | 7/2008 | Huber et al. | .................... | 602/30 |
| 2003/0005601 A1 | 1/2003 | Kasahara | | |
| 2006/0276737 A1 * | 12/2006 | Rose | ................................ | 602/30 |
| 2008/0262403 A1 | 10/2008 | Martin | | |
| 2010/0168632 A1 * | 7/2010 | Abbassian | .............. | A61F 5/019 |
| | | | | 602/30 |
| 2010/0249686 A1 * | 9/2010 | Rushton | .................. | A61F 5/019 |
| | | | | 602/30 |
| 2010/0249687 A1 * | 9/2010 | Goswami | ................ | A61F 5/019 |
| | | | | 602/30 |
| 2012/0215147 A1 * | 8/2012 | Lunnon | ................... | A61F 5/019 |
| | | | | 602/30 |
| 2012/0232453 A1 * | 9/2012 | Cropper | .................. | A61F 5/019 |
| | | | | 602/30 |
| 2013/0079694 A1 * | 3/2013 | Aquino | ........................... | 602/30 |
| 2013/0276331 A1 * | 10/2013 | Steel | ................................ | 36/94 |

FOREIGN PATENT DOCUMENTS

| | | | |
|---|---|---|---|
| FR | 2695028 A1 | | 3/1994 |
| FR | 2892298 A1 | | 4/2007 |
| FR | 2895235 A1 | | 6/2007 |
| JP | 2000116696 A | * | 4/2000 |
| WO | 2008102405 A1 | | 8/2008 |

OTHER PUBLICATIONS

Int'l Preliminary Report on Patentability issued Sep. 18, 2012 in Int'l Application No. PCT/IB2011/051013.

* cited by examiner

ORTHOPEDIC DEVICE FOR MECHANICAL TREATMENT OF HALLUX VALGUS

CROSS-REFERENCE TO RELATED APPLICATIONS

This application is a Section 371 of International Application No. PCT/IB2011/051013, filed Mar. 10, 2011, which was published in the French language on Sep. 15, 2011, under International Publication No. WO 2011/111019 A1, the disclosure of which is incorporated herein by reference.

BACKGROUND OF THE INVENTION

The present invention relates to an orthopedic device for mechanical treatment of Hallux Valgus by re-alignment thereof. This device can be worn both by day (with shoes) and by night.

Hallux Valgus is a deformation of the foot characterized by lateral inflexion of the big toe towards the other toes (abduction movement compared to the axis of the body) with the first metatarsal moving closer to the axis of the body (adduction), thus creating an increased angle between the first and the second metatarsal. Due to these two components, the first metatarsal makes an angle with the first phalanx of the big toe, the top of which creates a protrusion, i.e. an area generally painful and generating friction.

People suffering from Hallux Valgus can wear wide and flexible shoes, specialist shoes or even shoes such as those taught, for example, in French patent application publication FR 2 895 235 A1. While these shoes indisputably relieve wearers, they do not re-align and repair the Hallux Valgus.

In order to correct the deviation of the big toe, separators are available on the market. There are various separators available in the market, i.e. paramedical separators, tailor-made by a chiropodist or manufactured industrially, or even separators that mechanically spread the toe open by means of hard and rigid materials in the form of rigid night splints, further restraining the first metatarsal and enabling a first mechanical re-alignment by frames. In all cases, these devices are worn either during the day with shoes (separators) or at night without shoes (splint with rigid frame).

Furthermore, French patent application publication FR 2 576 209 A1 provides a device which can be worn with shoes, holding the foot by making a slight and progressive pull, thus enabling the big toe and the other toes of the foot to be re-aligned. This device consists of an orthopedic insole, which is associated with a mobile blade, enabling the pull of the big toe using a leather strap and fixed by means of a loop-and-hook fixing device, known by the brand name Velcro™, either under the sole of the arch of the foot or around the ankle.

While this orthopedic insole, which has the size of an insole, can be worn with shoes, it is unlikely that it fits into all types of shoes, more particularly the narrow and tight shoes mainly worn by women. Furthermore, the insole forms a sort of rigid splint that is not pleasant for the wearer. In addition, the device of FR 2 576 209 A1 can only be worn bare foot, without socks.

BRIEF SUMMARY OF THE INVENTION

The object of the present invention is to overcome the aforementioned disadvantages by providing an orthopedic device for the treatment of Hallux Valgus constituting a thin splint that is flexible and non-rigid, and can be worn with any type of shoes.

Another object of the invention is to provide a device which, by retention or restraining effect in particular, relieves the wearer.

Another object of this invention is to provide such a device that does not hinder the dynamics of the foot when walking, but which, on the contrary, uses such dynamics to re-align the Hallux Valgus.

Other goals and advantages will be seen in the following description which is given as a guide only and is not intended to limit it.

Therefore, some embodiments relate to an orthopedic device for the treatment of Hallux Valgus, the device being compatible with shoes, consisting essentially of a sleeve comprising: a main part intended to fit the foot locally on the metatarsals of the foot, a distal part for encapsulating the big toe, and a connecting band between the main part and the distal part, intended to be positioned laterally to the foot to be tensioned in order to exert a lateral force on the big toe that is directed inwards in relation to the axis $\Delta$ of the human body. According to one embodiment, the sleeve is an elastic sleeve intended to be worn on the foot to exert a localized restraining effect on the metatarsals of the foot, and a pad is secured onto the inner wall of the elastic sleeve, creating a localized increased thickness, the pad being arranged to be positioned laterally to the foot, locally against the first metatarsal of the big toe so as to act as an anchor during the application of the lateral force, the pad being capable of being placed in different positions of the foot so as to be able to adjust the tensile force on the connecting band.

According to one embodiment, the pad has a thickness between 2 mm and 7 mm, a length between 4 cm and 6 cm and a width between 2 cm and 4 cm.

According to one embodiment, the pad is made of a material having a friction coefficient such that the pad is in contact with the skin of the foot, without slipping, under the pressure of the restraining effect exerted by the sleeve.

According to one embodiment, the pad is secured inside the sleeve on the connecting band and on the main part of the sleeve, the pad being made of an elastic material so as to be capable of being stretched and keeping its stretch by contact with the skin of the foot, without slipping, so as to contribute to exerting the lateral force on the big toe.

According to one embodiment, the material of the pad is neoprene or silicone, or silicone gel.

According to one embodiment, the silicone gel forming the material of the pad in contact with the skin comprises an active ingredient capable of being transmitted by contact to the skin.

According to one embodiment, the device has a proximal part intended to press against the rear part of the foot to hold the elastic sleeve on the foot.

According to one embodiment, the proximal part is produced by a loop of the elastic sleeve, intended to be positioned around the ankle of the foot.

According to one embodiment, the pad is secured to the elastic sleeve permanently or using removable fixing means.

According to one embodiment, the removable fixing means comprise a pocket formed in the elastic sleeve, capable of receiving the pad in a removable manner, or comprise a loop-and-hook fixing system between the pad and the elastic sleeve.

According to one embodiment, the distal part is pre-formed so as to encapsulate the big toe without being in contact with the skin of the big toe in lateral edge regions of the nail of the big toe, in the absence of tensile force exerted on the connecting band, in order to limit the pressure exerted by the orthosis on the skin of the big toe in the lateral edge regions of the nail, in the presence of a tensile force exerted on the connecting band.

According to one embodiment, the elastic sleeve is made of an elastic textile such as elasthane.

According to one embodiment, the distal part and the connecting band are made of an elastic textile that is less stiff than the textile forming the main part of the sleeve.

According to one embodiment, the elastic sleeve is made from a textile pattern after sewing operations.

According to one embodiment, the elastic sleeve has a thickness of less than 1 mm.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 3 is a top view representing the device in a configuration spread open using the hands to enable the foot to pass into the device;

FIG. 4 is a top view showing the fitting of a main part of the device on the foot around the metatarsals;

FIGS. 5 and 6 are perspective views showing the step of encapsulating the big toe by a distal part of the device;

FIG. 7 is a partial top view of the device on the front part of the foot when correctly worn;

FIG. 8 is a side perspective view showing a step in which a tensile force exerted by the device is decreased;

FIG. 9 is a side perspective view in which the tensile force exerted by the device is increased;

FIG. 10 is a top perspective view showing the fitting of a proximal part of the device around the ankle;

Figure 16A:
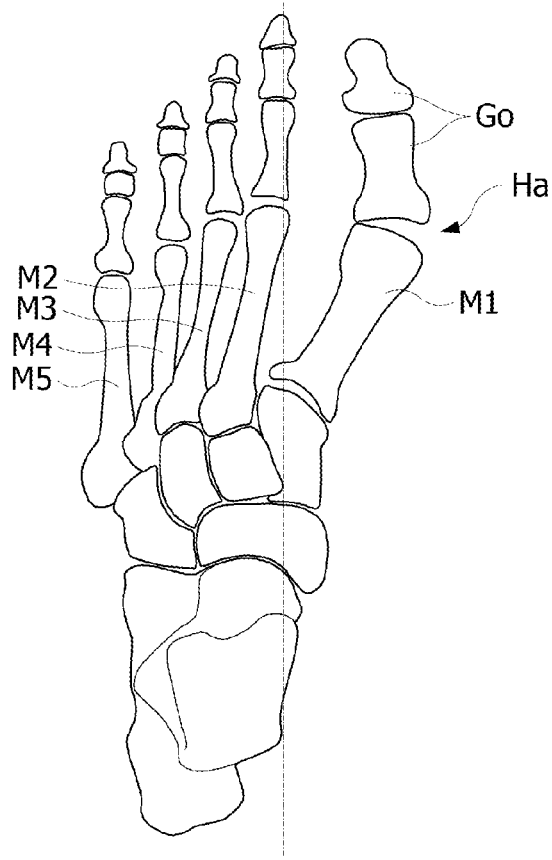
FIGS. 16A, 16B are two top views of the bone structure of a foot suffering from Hallux Valgus, respectively without and with the device.
Figure 16B:
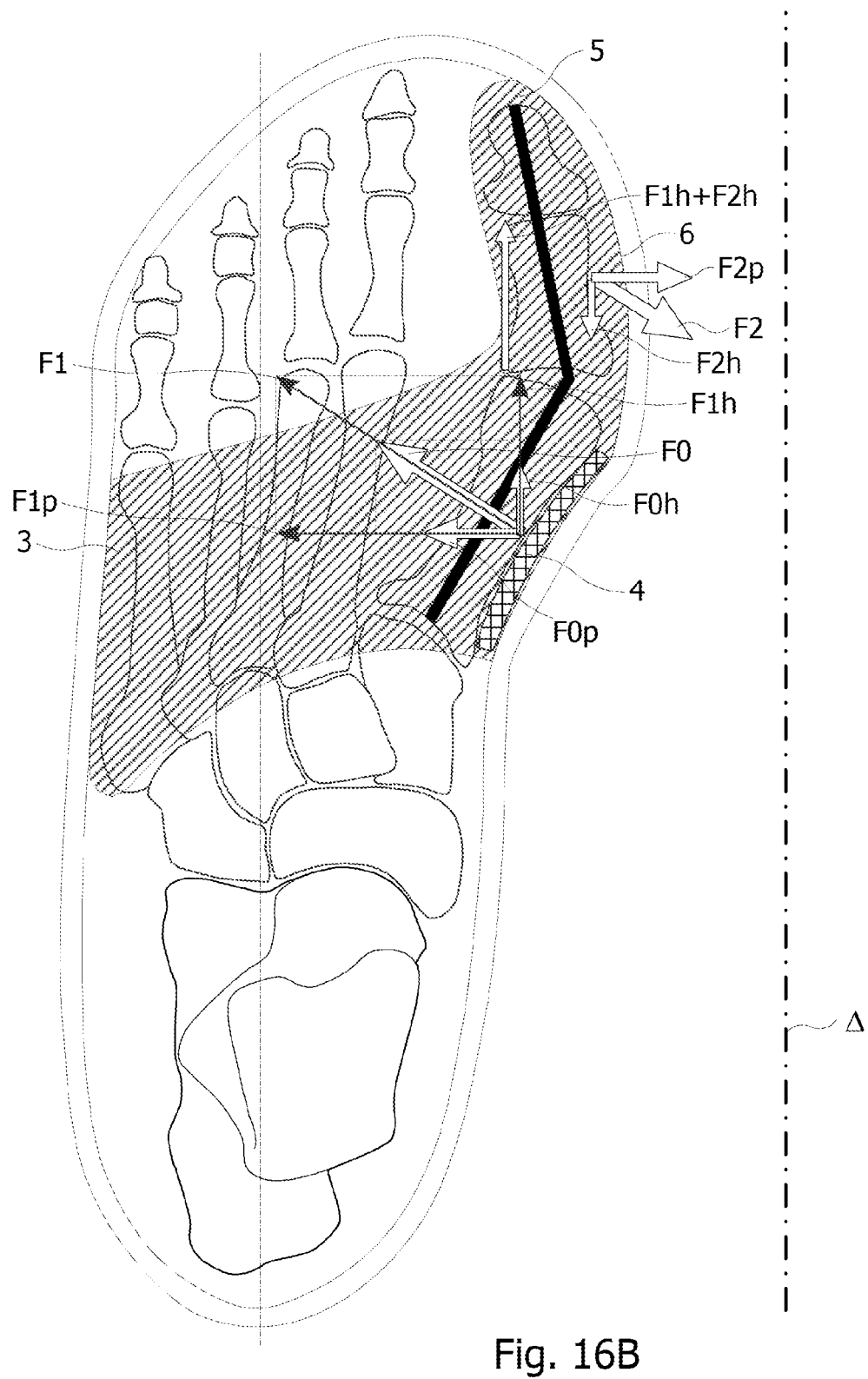

In the present application, the terms "inwards" and "outwards" used to describe the direction of forces, in particular, take the axis Δ of the human body as reference (see FIGS. 16A, 16B). The axis Δ of the human body is embodied by the plane of symmetry of the human body. When the force is directed toward this axis Δ, it is said to be directed inwards. When the force is directed in the other direction and deviates from the axis Δ, it is said to be directed outwards.

DETAILED DESCRIPTION OF THE INVENTION

Figure 1:
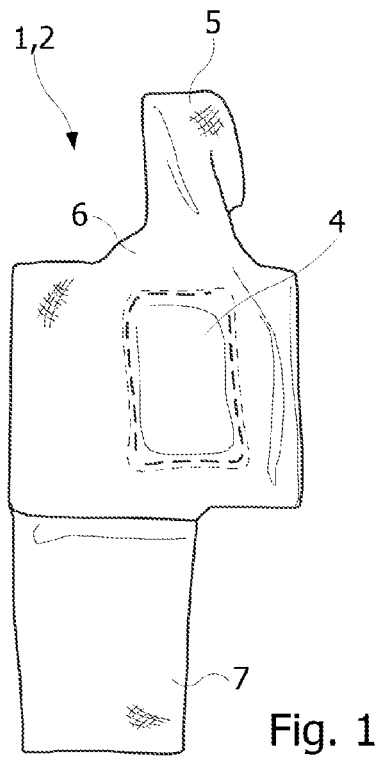
FIG. 1 is a side view of a device according to one embodiment of the invention, not worn.
Figure 2:
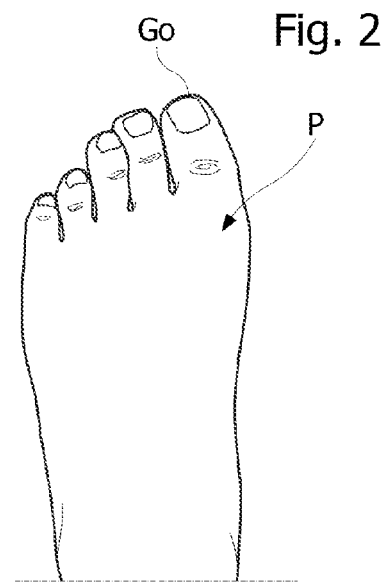
FIG. 2 is a top view of a foot on which the device of the invention will be worn.

FIGS. 1 and 16B represent an orthopedic device 1 for the treatment of Hallux Valgus Ha, essentially consisting of an elastic sleeve 2 intended to be worn on the foot P to exert a localized restraining effect on the metatarsals M1, M2, M3, M4, M5 of the foot (FIG. 16A). This restraining effect particularly enables the adduction of the first metatarsal M1 to be restricted compared to the axis Δ of the human body. The device 1 is flexible and non-rigid.

According to one embodiment, the localized restraining effect enables a lateral force F1 directed outwards in relation to the axis Δ of the human body to be exerted on the first metatarsal M1 of the big toe, i.e. towards the interior of the foot, so as to obtain a re-alignment of the metatarsus varus and thus of Hallux Valgus.

The device 1 is in the form of a thin splint, the thickness of which is substantially equal to that of the material of the sleeve, for example less than 1 mm, producing a slight restraining effect, relieving the user, and which can be worn continuously with any type of footwear. As the device 1 is no more cumbersome than a thin sock, it can be worn with any type of footwear, under stockings or socks in particular.

The device 1 comprises an elastic sleeve 2 whose primary function is to move the first metatarsal M1 of the big toe closer to the axis of the foot (and thus to distance the first metatarsal M1 from the axis Δ of the human body). This passive mechanical action is made possible at least by the elasticity of the sleeve 2 and is intended to fight against the metatarsus varus associated with the valgus of the big toe.

The elastic sleeve 2 can be made of a textile. It can be made from a pattern, particularly according to the size of the foot, after sewing operations. The textile of the flexible elastic sleeve 2 may comprise elasthane fibers giving the textile its elasticity. For example, the textile may be Lycra®.

Figure 15:
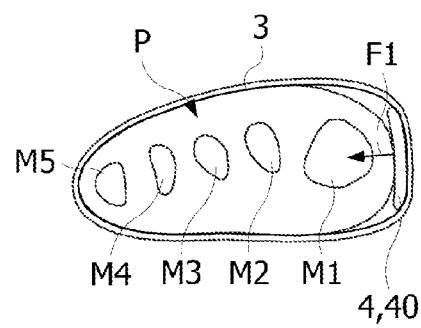
FIG. 15 is a front cross-sectional view at the metatarsal blade of the device worn on the foot, showing the cooperation between the pad and the first metatarsal of the big toe.
Figure 17:
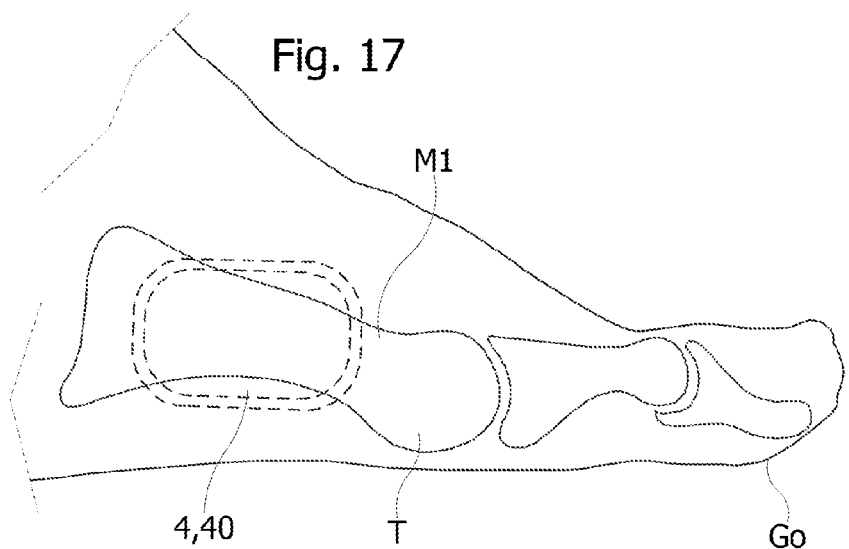
FIG. 17 is an inside lateral cross-sectional view showing by transparency the ideal positioning (in dotted lines) of the pad in relation to the first metatarsal of the big toe.

The device 1 comprises a pad 4, on the inner wall of the elastic sleeve 2, creating a localized increased thickness intended to be positioned laterally to the foot, locally against the first metatarsal M1 of the big toe, as shown in FIGS. 15, 16B and 17.

Advantageously, the pad 4 presses on the first metatarsal M1 and decreases the adduction of the latter in a progressive manner during the valgus thrust of the foot so as to propel it in line with the big toe.

As shown in FIG. 17, the dimensions of the pad 4 (in dotted lines) correspond substantially to the dimensions of the first metatarsal M1. The length of the pad 4 is slightly shorter than the length of the diaphysis of the first metatarsal, so as to allow a positioning of the pad 4 in different positions along the diaphysis of the first metatarsal, without covering the top T of the latter.

When the device is worn, the pad 4 is wedged against the inner wall of the shoe, thus increasing the lateral force F1, in order to re-align the first metatarsal M1 of the big toe.

Advantageously, as shown in FIG. 17, the pad 4 does not overlap the top T of the first metatarsal M1 so as to relieve the protrusion of the Hallux Valgus, which otherwise is often pressed against the inner wall of the shoe.

According to one embodiment, the device enables a lateral force F2 directed inwards compared to the axis Δ of the human body to be exerted on the big toe Go, at least indirectly, i.e. outwards in relation to the foot, the big toe resting on the next toe.

Figure 4:
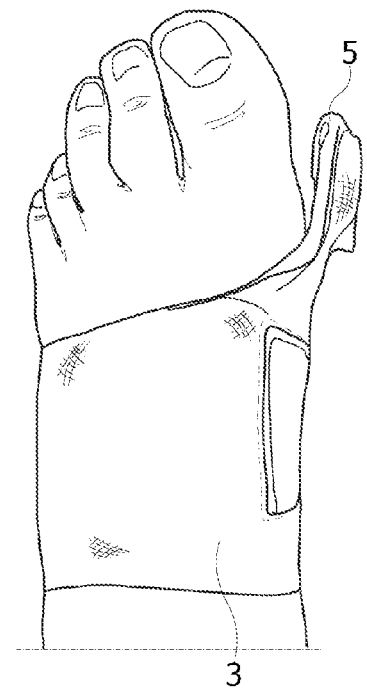

According to one embodiment shown by FIGS. 1 and 4, the elastic sleeve 2 comprises, in addition to a main part 3 intended to elastically fit the foot locally on the metatarsals M1, M2, M3, M4, M5 of said foot by hugging them tightly to exert on the first metatarsal M1 of the big toe Go the lateral force F1 directed outwards in relation to the axis Δ of the human body, a distal part 5 for encapsulating the big toe Go, as well as a connecting band 6 between the main part 3 and the distal part 5.

The distal part 5 holds the connecting band 6 laterally along the big toe Go to enable it to be tensioned, so as to increase the lateral force F2 directed inwards in relation to the axis Δ of the human body.

Figure 3:
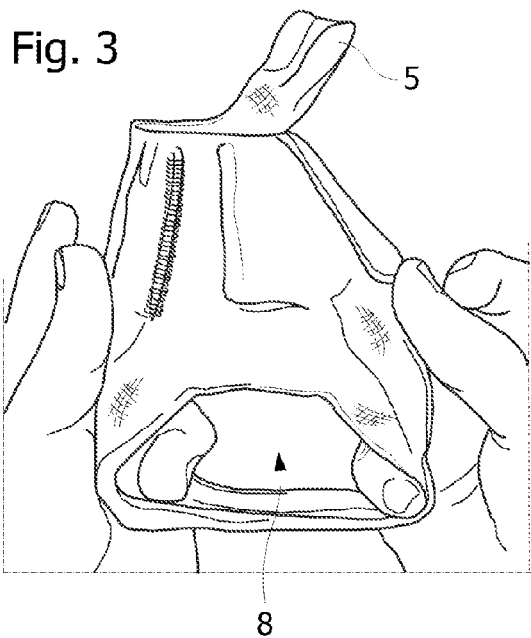
FIGS. 3 to 10 are views showing various steps of fitting the device shown in FIG. 1 on the foot shown in FIG. 2, and more particularly.
Figures 5, 6:
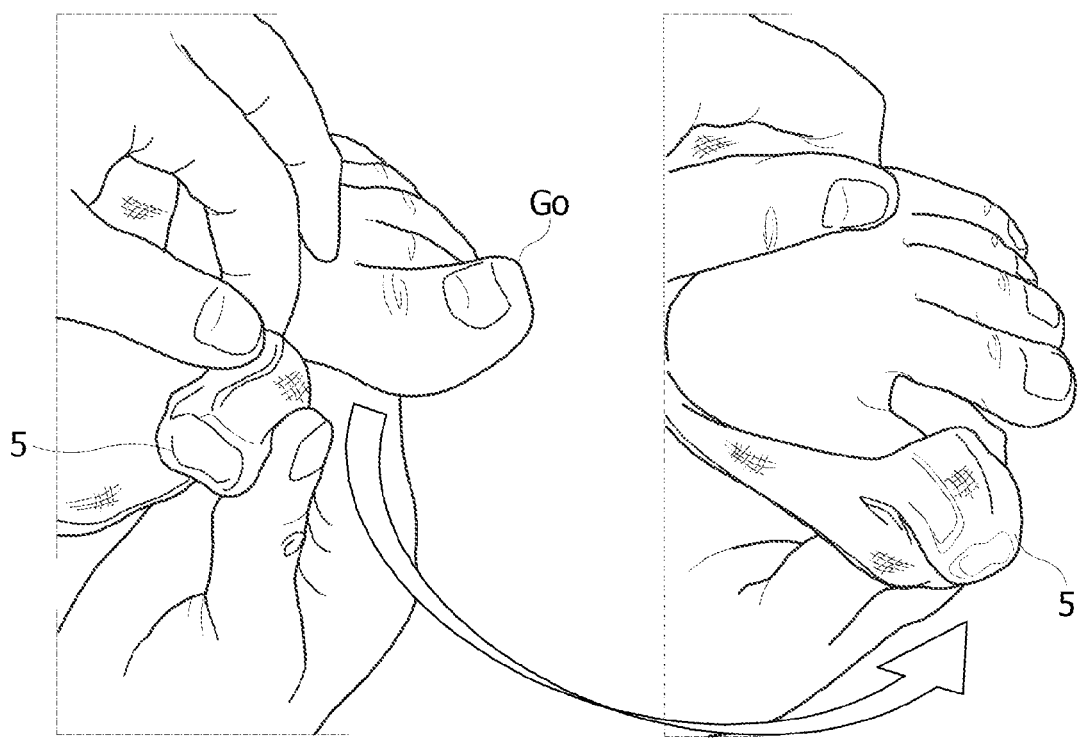
Figure 7:
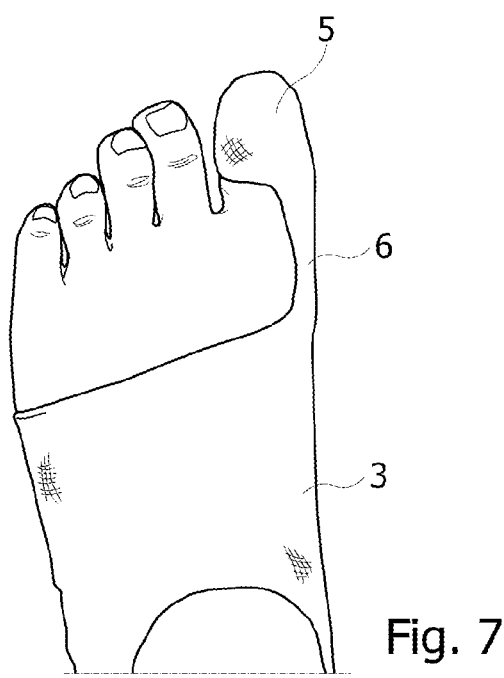

FIGS. 3 to 6 show various steps of fitting the device 1. In FIG. 3, the elastic sleeve 2 is spread open using the hands to widen the passage 8 of the foot into the sleeve and thus enable the front of the foot to be introduced into the sleeve. In FIG. 4, the sleeve 2 is positioned so as to surround the metatarsals M1-M5, and thus apply a restraining effort to them. In FIG. 5, the distal part 5 forming a cap is pulled towards the end of the big toe Go. In FIG. 6, the distal part 5 is engaged on the big toe Go. In FIG. 7, the device 1 is shown in a final position on the foot.

Figure 11:
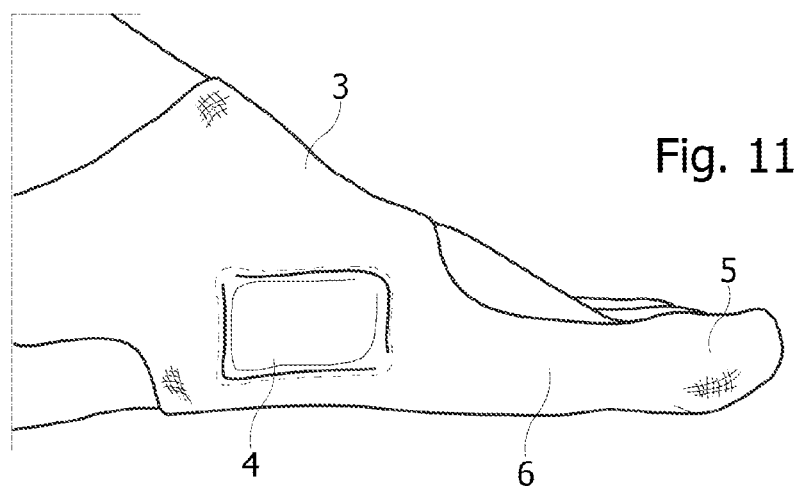
FIG. 11 is an inside lateral view of the device when correctly worn on the foot.
Figure 12:
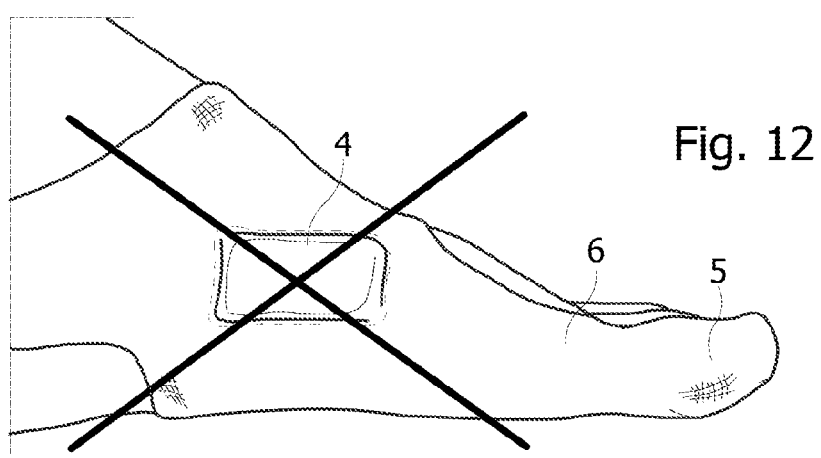
FIG. 12 is an inside lateral view of the device when worn too high on the foot.
Figure 13:
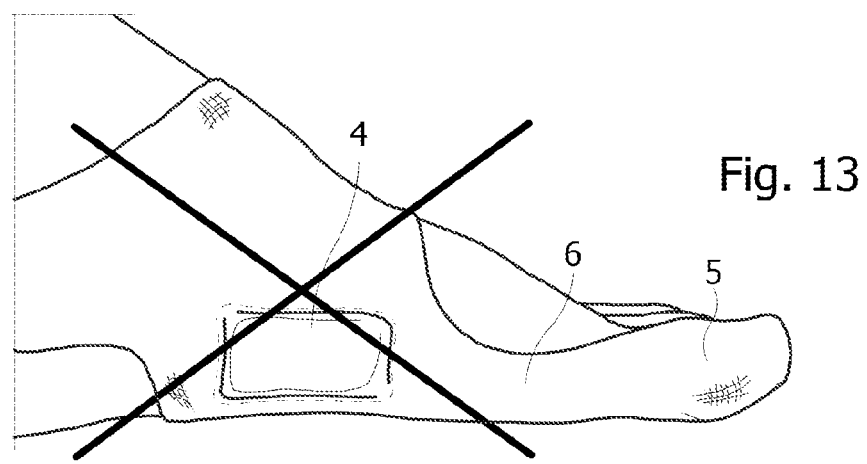
FIG. 13 is an inside lateral view of the device when worn too low on the foot.

As shown in FIG. 11, the connecting band 6 must be positioned laterally along the big toe Go and the first metatarsal in the axis of the big toe and not in an excessively high position as shown in FIG. 12 or even too low as shown in FIG. 13.

Advantageously, the device can further have means of setting the lateral force F2 exerted on the big toe Go. The means of setting the force F2 can consist of the pad 4 previously described. For this purpose, the pad 4 is made of a material 40 having a sufficient friction coefficient to be directly in contact with the skin of the foot, without slipping. In other words, the pad 4 adheres to the skin. This adherence can be made possible by the restraining force exerted by the part 3 of the sleeve 2, which is also exerted on the pad 4.

Figures 8, 9:
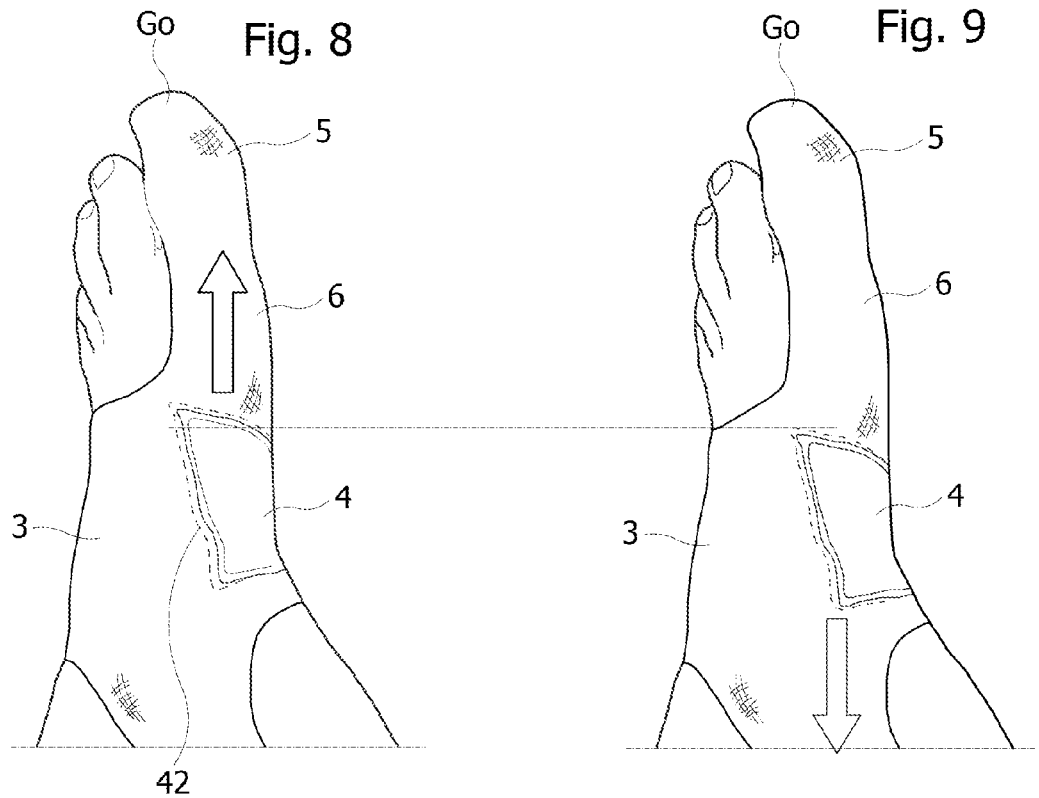

Therefore, as shown in the examples of FIG. 8 or 9, the pad 4 can be placed in different positions of the foot so as to be able to adjust the tensile force on the connecting band 6. In FIGS. 8 and 9, the position of the pad is visible by the seams 42 joining the material, particularly textile, of the elastic sleeve 2 around the edge of the pad.

As shown in FIG. 8, the pad 4 is moved closer to the big toe Go, so as to decrease the tensile force on the connecting band 6, and thus decrease the lateral force F2 on the big toe. In contrast, as shown in FIG. 9, the pad 4 is moved away from the big toe Go, so as to increase the tensile force on the connecting band 6 and thus the tension of the connecting band, and thus increase the lateral force F2 exerted on the big toe. Adjusting the position of the pad 4 along the first metatarsal M1 thus enables the tension of the connecting band 6 to be adjusted.

As shown in FIG. 16B, the main part 3 of the sleeve, by holding the five metatarsals M1-M5 tight, exerts a force F0 that is broken down along axes parallel to the axis of the foot and perpendicular to the axis of the foot, into an axial force component F0$h$ and a lateral force component F0$p$. The presence of the pad 4 intensifies the force F0, particularly during walking and when the person is wearing shoes. The resulting force corresponds to the force F1 previously mentioned. The force F1 can also be broken down into an axial component F1$h$ and a lateral component F1$p$.

Furthermore, when the user moves the pad 4 towards the heel by pulling the connecting band 6, this creates the force F2 which can also be broken down into an axial component F2$h$ and a lateral component F2$p$. In these conditions, the big toe Go and the first metatarsal M1 undergo a resulting force equal to F1$h$+F2$h$, the component F2$h$ being adjustable. Furthermore, the components F1$p$ and F2$p$ act in combination to reduce the Hallux Valgus, the component F2$p$ being adjustable.

During walking, it can be seen that the component F1$p$ of the force F1 increases upon the development of each step, when the foot exerts a thrust, and that this component decreases when the foot leaves the ground. The bones which converge towards the joint (metatarsus M1 and phalanx of the big toe) are subjected by the device 2 to variable moments of force tending to reduce the Hallux Valgus. The resulting motions are of the same nature as those that could be done by a physiotherapist and occur naturally and gently during walking.

According to one embodiment, the material 40 can be, for example, neoprene or silicone elastomer or even silicone gel. The pad 4 is made, for example, of a band having a thickness between 2 and 7 mm for example, a length between 4 and 6 cm, and a width between 2 and 4 cm.

The pad 4 can be secured permanently to the elastic sleeve 2 (for example by sewing, gluing, etc.). Alternatively, so as to be able to wash the material, particularly the textile material, of the elastic sleeve 2, the pad 4 can be separated from the sleeve 2 by providing removable fixing means (not shown) between the pad 4 and the elastic sleeve 2.

For example, the removable fixing means can comprise a pocket capable of receiving the pad 4 in a removable manner. This pocket can have a window opposite the foot, so as to allow direct contact between the non-slipping material 40 (setting means) of the pad 4 and the foot P. Alternatively, the removable fixing means can be made of a loop-and-hook fixing system between the pad 4 and the elastic sleeve 2.

The removable nature of the pad 4 can be advantageous to use pads of different thicknesses so as to adjust the force F1 (and thus the component F1$p$) exerted on the first metatarsal M1 depending on the extent of the metatarsus varus, and/or depending on the development thereof, including in the event of reduction. It is indeed well known that the flexibility of a joint depends largely on the learning from which it benefits. Therefore, an increasing tolerance to the corrective forces can be observed as the orthosis is used, which can warrant the use of thicker and thicker materials.

Figure 10:
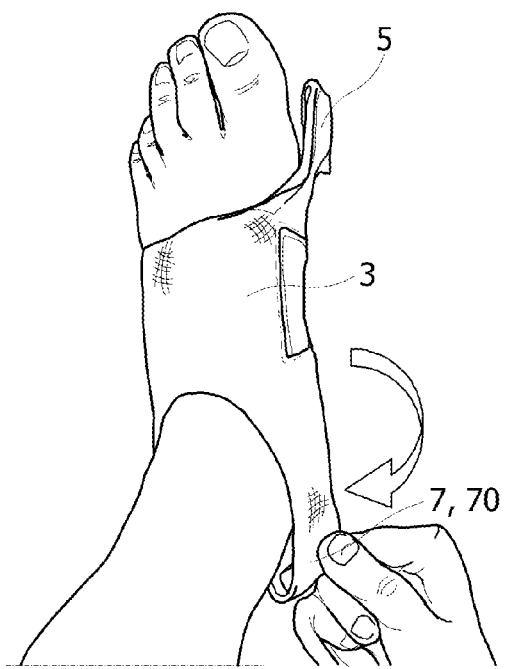
Figure 14:
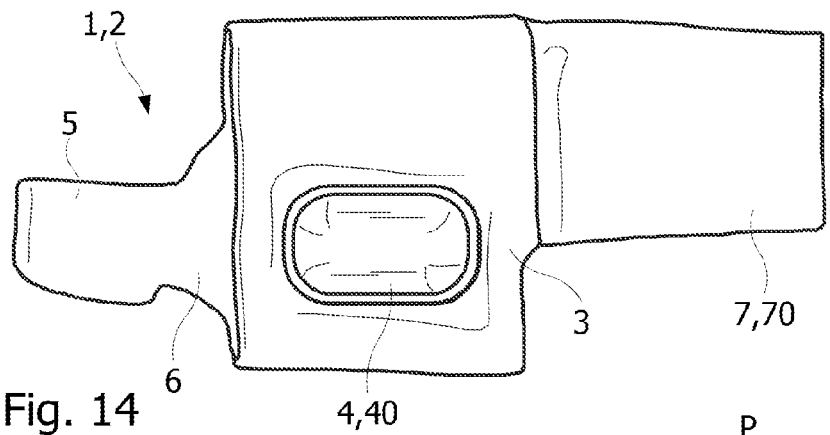
FIG. 14 is a view of the device, in the rolled up state, enabling an internal pad to be seen.

According to one embodiment shown in FIGS. 1, 7 and 14, the device can further comprise a proximal part 7 intended to press on the rear part of the foot P to hold the elastic sleeve 2 on the foot P. The proximal part 7 is produced by a loop 70 formed by the elastic sleeve, intended to be positioned around the ankle of the foot P, as shown in FIG. 10.

Figure 18:
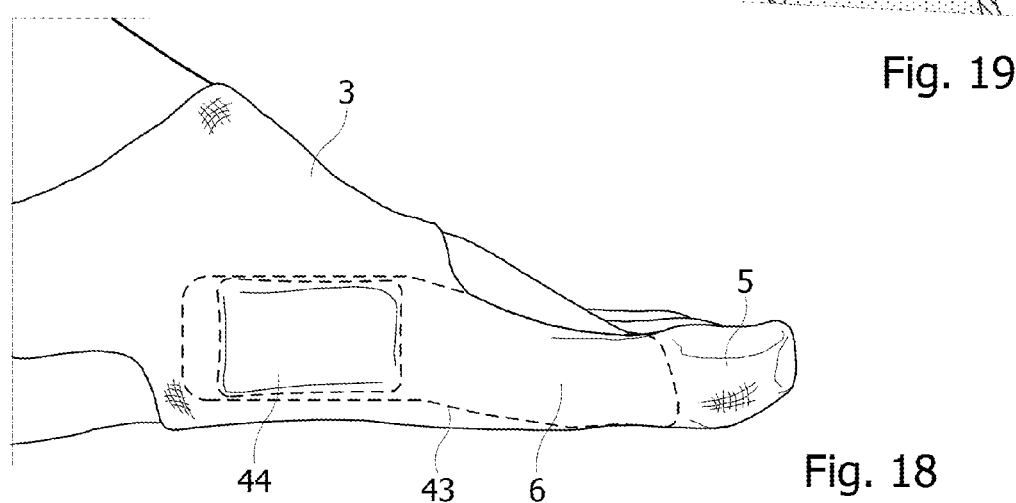
FIG. 18 is an inside lateral view representing an orthopedic device according to another embodiment of the invention.

According to one embodiment shown in FIG. 18, the pad 4 is replaced with a pad 43 in the form of an elastic band. The pad 43 is secured inside the sleeve 2 where the pad 4 is located, on the connecting band 6, up to the distal part 5. The band 43 has a friction coefficient with the skin, such that it can be stretched and keep such stretch by contact with the skin of the foot without slipping. By pulling the part 3 of the sleeve 2 in a proximal direction to distance it from the distal part 5, the band 43 stretches with the connecting band 6 and the part 3 and remains in its final stretched configuration due to its adherence to the skin. Therefore, the elastic band 43 performs both the functions of increasing, thanks to its thickness, the restraining force F1 exerted on the metatarsal M1, of anchoring thanks to its friction coefficient with the skin, to exert and adjust the force F2, and of contributing thanks to its elasticity with the connecting band 6 and the part 3 of the sleeve 2 to the amplitude of the force F2. The pad 43 can be secured to the part 3 of the sleeve 2 and to the connecting band 6, for example by sewing or by gluing.

According to one embodiment, the pad and anchor functions, to exert the force F2, are separated by providing that the pad 43 secured inside the sleeve 2 has a low thickness, and by providing an additional pad 44 secured between the pad 43 and the part 3 of the sleeve 2. The pad 44 can be identical to the pad 4.

According to one embodiment, the pad 43 and/or 44 is made of neoprene or silicone elastomer, or even of a polymer gel, such as a silicone gel.

Figure 19:
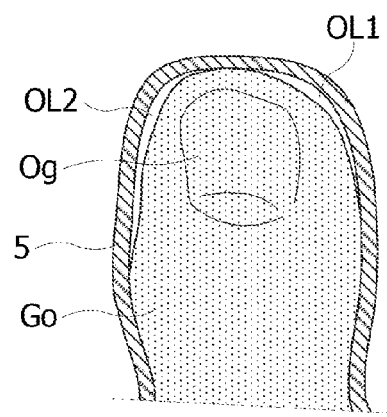
FIG. 19 is a top cross-sectional view representing the distal part of a device according to one embodiment of the invention.

According to one embodiment shown in FIG. 19, the distal part 5 is pre-formed so as not to fit the shape of the big toe Go exactly, and not to come into contact with the skin of the big toe in lateral edge regions OL1, OL2 of the nail Og of the big toe Go (in the absence of tensile force exerted on the connecting band 6). This arrangement restricts the pressure exerted by the orthosis, in the presence of a tensile force exerted on the connecting band 6, on the skin in the lateral edge regions of the nail of the big toe, and thus increases the user's comfort.

According to one embodiment, the sleeve 2 is made of a fabric different from those of the connecting band and the distal part 5. Therefore, the elastic fabric of which the sleeve 2 is made can be stiffer than that of the band 6 and the distal part 5, to obtain a significant restraining effect without causing any discomfort in the area of the big toe which is more sensitive.

It shall be noted that the slighter stiffness of the connecting band 6 can be offset by the presence of the elastic band 43. The cooperation between the connecting band 6 and the elastic band also plays a role in maintaining the elastic function over time. Fabrics effectively always tend not to regain their exact initial length after stretching, which is not the case of the silicone gel bands used. In the absence of the band 43, for the same force, the position of the pad 4 would move towards the heel to the point that it would lose its useful position, just behind the joint.

In another embodiment, with or without the elastic band 43, the sleeve can be made of a single piece of fabric having a slighter stiffness in the direction of the extension of the connecting band 6 than in the direction of the widening of the main part 3, to exert a significant restraining force on the metatarsals, without any discomfort in the area of the end of the big toe.

According to one embodiment, the property of the silicone gels to absorb oily products can be used to diffuse active ingredients into the skin. Therefore, the pad 4 or the band 43 can contain an active ingredient to be diffused by contact with the skin. The active ingredient can be chosen, for example, to relieve pain or to provide treatment. The active ingredient can be introduced into the silicone gel several times, merely by pouring it onto the pad 4 or the elastic band 43.

Naturally, other embodiments can be considered by those skilled in the art while remaining within the framework of the invention defined by the claims below.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An orthopedic device for treating Hallux Valgus, the orthopedic device consisting essentially of a sleeve comprising:
    a main part shaped to fit a foot of a human body locally around metatarsals of the foot, a distal part shaped to encapsulate a big toe of the foot, and
    a connecting band between the main part and the distal part shaped to be positioned laterally on the foot,
    wherein the sleeve is an elastic sleeve shaped to be worn on the foot to exert a localized restraining effect on the metatarsals of the foot and being compatible with wearing of a shoe on the foot, and
    wherein a first pad is secured on an inner wall of the elastic sleeve to be positioned laterally to the foot and locally against skin of the foot along a first metatarsal of the big toe, the first pad comprising a material having a friction coefficient for preventing the first pad, positioned against the skin, from slipping when the elastic sleeve is worn on the foot and pressure is exerted by the main part of the sleeve around the metatarsals, a position of the first pad along the first metatarsal being adjustable to adjust elastic elongation of the connecting band and thereby adjust a tensile force exerted by the connecting band between a lateral side of the first metatarsal and a tip of the big toe.

2. The orthopedic device according to claim 1, wherein the first pad is shaped to extend along the first metatarsal without covering a top of the first metatarsal when the elastic sleeve is worn on the foot, and has a thickness between 2 mm and 7 mm, a length between 4 cm and 6 cm, and a width between 2 cm and 4 cm.

3. The orthopedic device according to claim 1, wherein the first pad secured on the inner wall of the sleeve extends along the connecting band from the distal part of the sleeve to the main part of the sleeve, the first pad comprising an elastic, stretchable material, maintaining its stretch by contact with skin of the foot, without slipping, to contribute to the tensile force exerted by the connecting band between the lateral side of the first metatarsal and the tip of the big toe.

4. The orthopedic device according to claim 3, further comprising a second pad secured between the inner wall of the elastic sleeve and the first pad, the second pad being positioned laterally to the foot and extending along the first metatarsal of the big toe without covering a top of the first metatarsal, when the elastic sleeve is worn on the foot.

5. The orthopedic device according to claim 4, wherein the second pad is removably secured to the elastic sleeve in a pocket formed between the elastic sleeve and the first pad, the pocket receiving the second pad in a removable manner.

6. The orthopedic device according to claim 4, wherein the second pad has a thickness between 2 mm and 7 mm, a length between 4 cm and 6 cm, and a width between 2 cm and 4 cm.

7. The orthopedic device according to claim 4, wherein a material of the second pad is selected from the group consisting of neoprene, silicone, and silicone gel.

8. The orthopedic device according to claim 1, wherein the material of the first pad is selected from the group consisting of neoprene, silicone, and silicone gel.

9. The orthopedic device according to claim 8, wherein the material of the first pad to be in contact with the skin comprises silicone gel containing an active ingredient capable of being transmitted by contact to the skin.

10. The orthopedic device according to claim 1, wherein the first pad is permanently secured to the elastic sleeve.

11. The orthopedic device according to claim 1, wherein the first pad is removably secured to the elastic sleeve by a loop-and-hook fixing system between the pad and the elastic sleeve.

12. The orthopedic device according to claim 1, wherein the distal part is pre-formed so as to encapsulate the big toe without being in contact with skin of the big toe in lateral edge regions of a nail of the big toe, in the absence of the tensile force exerted on the connecting band, so as to limit pressure exerted by orthosis on the skin of the big toe in the lateral edge regions of the nail, when a tensile force is exerted on the connecting band.

13. The orthopedic device according to claim 1, wherein the elastic sleeve comprises an elastic textile.

14. The orthopedic device according to claim 13, wherein the elastic textile comprises elasthane.

15. The orthopedic device according to claim 1, wherein the distal part and the connecting band comprise an elastic textile that is less stiff than a textile forming the main part of the sleeve.

16. The orthopedic device according to claim 15, wherein the elastic sleeve comprises a textile pattern after sewing operations.

17. The orthopedic device according to claim 1, wherein the elastic sleeve has a thickness of less than 1 mm.

18. An orthopedic device for treating Hallux Valgus, the orthopedic device consisting essentially of a sleeve comprising:
a main part shaped to fit a foot of a human body locally around metatarsals of the foot, a distal part shaped to encapsulate a big toe of the foot, and
a connecting band between the main part and the distal part shaped to be positioned laterally on the foot,
wherein the sleeve is an elastic sleeve shaped to be worn on the foot to exert a localized restraining effect on the metatarsals of the foot and being compatible with wearing of a shoe on the foot, and
wherein a pad is secured on an inner wall of the elastic sleeve to be positioned laterally to the foot against skin of the foot and shaped to extend along a first metatarsal of the big toe without covering a top of the first metatarsal, the pad comprising a material having a friction coefficient preventing the pad positioned against the skin of the foot from slipping, under pressure exerted by the main part of the sleeve around the metatarsals, when the elastic sleeve is worn on the foot, a position of the pad along the first metatarsal and elastic elongation of the connecting band being adjustable to adjust a tensile force exerted by the connecting band between a lateral side of the first metatarsal and a tip of the big toe.

19. The orthopedic device according to claim 18, wherein the first pad has a thickness between 2 mm and 7 mm, a length between 4 cm and 6 cm, and a width between 2 cm and 4 cm.

20. The orthopedic device according to claim 18, wherein the pad is permanently secured to the elastic sleeve.

21. The orthopedic device according to claim 18, wherein the pad is removably secured to the elastic sleeve by a loop-and-hook fixing system between the pad and the elastic sleeve.

22. The orthopedic device according to claim 18, wherein the distal part is pre-formed so as to encapsulate the big toe without being in contact with skin of the big toe in lateral edge regions of a nail of the big toe, in the absence of the tensile force exerted on the connecting band, so as to limit pressure exerted by orthosis on the skin of the big toe in the lateral edge regions of the nail, when a tensile force is exerted on the connecting band.

23. The orthopedic device according to claim 18, wherein the elastic sleeve has a thickness of less than 1 mm.

24. The orthopedic device according to claim 18, wherein the material of the pad is selected from the group consisting of neoprene, silicone, and silicone gel.

25. An orthopedic device for treating Hallux Valgus, the orthopedic device comprising a sleeve, a thin pad and a thick pad, the sleeve comprising:
a main part shaped to fit a foot of a human body locally around metatarsals of the foot, a distal part shaped to encapsulate a big toe of the foot, and
a connecting band between the main part and the distal part shaped to be positioned laterally on the foot,
wherein the sleeve is an elastic sleeve shaped to be worn on the foot to exert a localized restraining effect on the metatarsals of the foot and being compatible with wearing of a shoe on the foot,
wherein the thin pad is secured on an inner wall of the elastic sleeve to be positioned laterally to the foot against skin of the foot and extends along the connecting band from the distal part of the sleeve to the main part of the sleeve, the thin pad comprising an elastic material having a friction coefficient preventing the thin pad positioned against the skin of foot from slipping under pressure exerted by the main part of the sleeve around the metatarsals, when the elastic sleeve is worn on the foot, the thin pad being stretchable with the connecting band to keep its stretch by contact with the skin of the foot, without slipping using the friction coefficient, and
wherein the thick pad is shaped and positioned between the sleeve and the thin pad to extend along a first metatarsal of the big toe without covering a top of the first metatarsal, a position of the thick pad along the first metatarsal and the elastic elongation of the connecting band and the thin pad being adjustable, to adjust a tensile force exerted by the connecting band and the thin pad between a lateral side of the first metatarsal and a tip of the big toe.

26. The orthopedic device according to claim 25, wherein the material of at least one of the thin pad and the thick pad is selected from the group consisting of neoprene, silicone, and silicone gel.

27. The orthopedic device according to claim 25, wherein a material of the thin pad to be in contact with the skin comprises silicone gel containing an active ingredient capable of being transmitted by contact to the skin.

28. The orthopedic device according to claim 25, wherein the thick pad is removably secured to the elastic sleeve in a pocket formed between the elastic sleeve and the thin pad, the pocket receiving the thick pad in a removable manner.

29. The orthopedic device according to claim 25, wherein the distal part is pre-formed so as to encapsulate the big toe without being in contact with skin of the big toe in lateral edge regions of a nail of the big toe, in the absence of the tensile force exerted on the connecting band, so as to limit pressure exerted by orthosis on the skin of the big toe in the lateral edge regions of the nail, when a tensile force is exerted on the connecting band.

30. The orthopedic device according to claim 25, wherein the elastic sleeve comprises an elastic textile.

31. The orthopedic device according to claim 30, wherein the elastic textile comprises elasthane.

32. The orthopedic device according to claim 25, wherein the distal part and the connecting band comprise an elastic textile that is less stiff than a textile forming the main part of the sleeve.

33. The orthopedic device according to claim 25, wherein the elastic sleeve has a thickness of less than 1 mm.

34. The orthopedic device according to claim 25, wherein the thick pad has a thickness between 2 mm and 7 mm, a length between 4 cm and 6 cm, and a width between 2 cm and 4 cm.

35. The orthopedic device according to claim 25, wherein a material of the thick pad is selected from the group consisting of neoprene, silicone, and silicone gel.

* * * * *